(12) United States Patent
Nunez

(10) Patent No.: US 7,000,491 B1
(45) Date of Patent: Feb. 21, 2006

(54) AQUEOUS VERTICAL SAMPLER

(75) Inventor: Jose Manuel Nunez, St. Augustine, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/961,560

(22) Filed: Oct. 8, 2004

(51) Int. Cl.
*G01N 1/00* (2006.01)

(52) U.S. Cl. .................................. 73/864.64; 73/864.67

(58) Field of Classification Search ............. 73/864.63, 73/864.64, 864.65, 865.66, 864.67, 864.52, 73/864.61, 864.04; 294/68.25, 68.21, 68.22
See application file for complete search history.

(56) References Cited

U.S. PATENT DOCUMENTS

| | | | | |
|---|---|---|---|---|
| 540,121 A | * | 5/1895 | Tagliabue | 73/864.65 |
| 1,585,072 A | * | 5/1926 | Banks | 73/864.63 |
| 2,059,999 A | * | 11/1936 | Rainville | 73/864.63 |
| 2,298,627 A | * | 10/1942 | Proudman et al. | 73/864.63 |
| 4,266,429 A | * | 5/1981 | Brovold | 73/864.63 |
| 4,583,293 A | * | 4/1986 | Smith | 33/717 |
| 4,594,905 A | * | 6/1986 | Roberts | 73/864.63 |
| 5,341,692 A | * | 8/1994 | Sher et al. | 73/864.63 |

OTHER PUBLICATIONS

Kahl Scientific Instrument Corporation. *Van Dorn Style Water Samplers*. Retrieved Sep. 13, 2004 on the World Wide Web: http://www.kahlsico.com/vandorn.html.

* cited by examiner

Primary Examiner—Robert Raevis
(74) Attorney, Agent, or Firm—McDonnell Boehnen Hulbert & Berghoff LLP

(57) ABSTRACT

A fluid sampling device is provided that can obtain both point and integrated samples of a body of fluid at various depths. The device includes an easy to use and reliable closure mechanism that does not rely on a traditional messenger mechanism.

8 Claims, 5 Drawing Sheets

AQUEOUS VERTICAL SAMPLER

FIELD OF THE INVENTION

My invention relates to an apparatus and method for sampling fluids. More specifically, the invention relates to an apparatus that can collect fluids at a single depth or across a range of depths for subsequent analysis.

BACKGROUND OF THE INVENTION

Fluid sampling devices, especially those used to collect aqueous samples from large bodies of fluids, for example, oceans and lakes, are well known. Such devices can be used to collect surface or near-surface physical, chemical, or biological (phytoplankton/zooplankton) samples in natural water bodies or industrial or man-made facilities (waste water ponds, water treatment plants, food processing plants, oxidation ponds, etc.) In particular, collection of water samples below the surface provides scientists the ability to obtain a sample at a known depth, retrieve the sample, and then perform analysis on the sample at a later point in time. By collecting a number of samples at various depths, a profile analysis of the body of fluid can be obtained. Unfortunately, existing sampling devices are cumbersome to use because their spring loaded closure designs require the use of a weighted messenger that must travel down a connecting line through the fluid and then trip a trigger that activates the closing mechanism. Such designs are known to frequently malfunction causing the device to close prematurely or to not close at all. Examples of these designs include three well known sampling bottles marketed under the names "Van Dorn," "Niskin," and "Kemmerer." Each of these designs relies on a spring-loaded cover or cap that must be triggered when the device is lowered to a specified depth. Another serious drawback of these known sampling bottles is that they can only obtain one kind of sample, either "point" samples, i.e., obtain only a single sample at a single depth when in horizontal position (e.g. "Van Dorn"), or "vertically integrated" samples when in the vertical position A need therefore exists for a reliable, fool-proof sampling device that can take both point samples and a composite or integrated sample across a range of depths. I have now created such a design and a method of using it as will be described herein.

SUMMARY OF THE INVENTION

My invention is a multipurpose vertical aqueous sampler and a method of using it to collect both point and integrated samples of fluids in bodies of fluids, such as rivers, ponds, swamps, lakes, oceans and the like. In one embodiment the sampling device of my invention comprises a tube or other hollow structure capable of holding a fluid sample. A stopper located at the bottom of the tube is connected to a central shaft that is used to open and close the stopper. A slotted sleeve is attached at the bottom end of the tube which allows fluid to enter the tube when the stopper is placed in an open or semi-open position. The sampling device also has two lines attached, one for lowering the tube in the body of fluid and one is attached to the shaft for toggling the stopper from an open to a closed position and for retrieving the device from the body of fluid.

The tube can be constructed of any material that can withstand immersion into the fluid being sampled. Preferably, the tube is constructed of a transparent material such as clear acrylic, glass, Plexiglas or other synthetic plastic material that allows for easy visual observation of a collected sample. Other materials such as PVC, metal or ceramics could be used if desired. The preferred shape of the tube is circular, but depending on the design of the stopper other shaped tubes (oval, square, triangular, etc.) will work equally well. The stopper must be designed to fit snugly into the bottom end of the tube when in the closed position to provide a tight seal and to prevent a collected sample from leaking out of the tube. A preferred material of construction of the stopper is rubber or other compressible material such as cork or a like material, however, the exact material of construction is not critical to the invention as long as it provides a tight seal and does not adversely affect the sample being collected through decay, dissolution or contamination. The slots in the sleeve allow the flow of fluid into the device when the stopper is placed in a open position. Partial opening of the stopper allows for a controlled flow of fluid into the device. My sampling device may optionally contain a sample port positioned at the lower end of the device. This sample port provides a convenient means to withdraw a measured portion of the acquired fluid sample for analysis. Likewise, the tube may optionally contain graduated markings that will signify the volume of a fluid inside the tube and/or the depth of sampling. My sampling device may optionally be outfitted with a ballast at the end of the slotted sleeve, attached to a removable holding ring. Use of the ballast is recommended when collecting water samples in waters with strong currents. Another optional feature is a set of two flaps at the top head of the sampler that automatically close upon retrieval of the sampler to help protect the integrity of the sample.

As mentioned, my invention also involves a method of using my sampling device to collect both point and integrated samples. To collect a point sample the stopper of my device is placed in the closed position. The device is then pushed down to a predetermined depth in a body of fluid (depth no more than the length of the sampler). Once the desired depth is reached, the stopper is opened to allow fluid to enter the tube through the slotted sleeve. Once the tube is filled with fluid the stopper is closed and the device is withdrawn from the body of fluid using a line attached to a shaft connected to the stopper. For collecting an integrated sample of fluid across a range of depths the stopper is first placed in an open position and then lowered into the body of fluid. As the sampler device descends, fluid enters the slotted sleeve and into the tube. When the bottom of the device reaches the final desired depth, the shaft is toggled to close the stopper to prevent further collection of fluid. With the stopper in the closed position the device can then be retrieved using a line attached to a shaft connected to the stopper The result of this method of sample collection is that small portions of fluids are collected beginning at the surface (or sub-surface) and continues as the device descends to a final depth. When the integrated sample collection method is used, two types of samples may be retrieved from the tube. If a composite of the fluid collected across the depth range is desired, then the stopper is opened and the entire contents of the tube is emptied and mixed into another container where single samples are taken for analysis. Alternatively, if a stratified sub-sampling analysis is desire, the tube is maintained in a vertical orientation after retrieval from the body of fluid (matching that of when the sample was collected) and placed in a deck stand to maintain that orientation with the stopper in the closed position. Single sub-samples can then be removed using the optional sample port located at the bottom of the tube. In this way the first samples taken from the sample port will represent fluid taken at the deepest depth of the depth range covered during the integrated sampling method.

The invention may take form in various parts and arrangement of parts. The drawings are only for purposes of illustrating preferred embodiments and are not to be construed as limiting the invention.

DESCRIPTION OF PREFERRED EMBODIMENTS

Reference will now be made to the Figures accompanying this application to further describe my invention.

Figure 1:
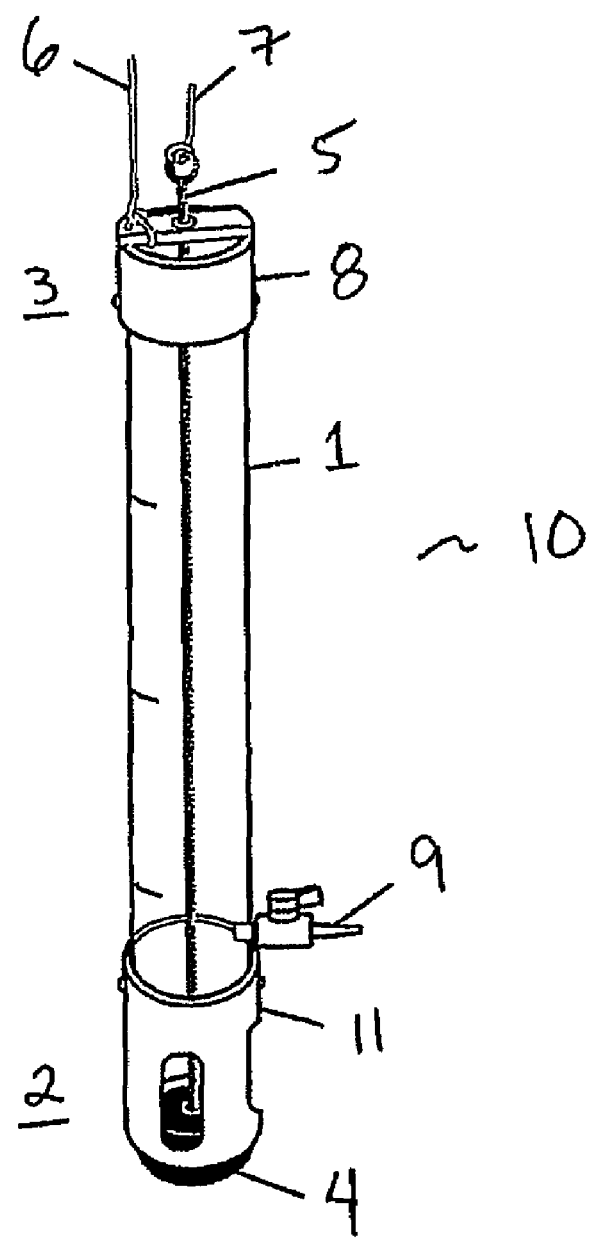
FIG. 1 shows a perspective view of one embodiment of my sampling device.

FIG. 1 shows sampling device 10 of my invention in a vertical orientation as it would be deployed to sample a body of fluids. A circular tube 1 has an upper end 3 and a lower end 2 and is shown connected to slotted sleeve 11. Optional sample port 9 is located at lower end 2. Stopper 4 is connected to shaft 5 at lower end 2 and is designed to slide easily, guided by the slotted sleeve 11. FIG. 1 shows the stopper in the open position where the slots in sleeve 11 provide an opening in the bottom end 2 of tube 1. Top head 8 is attached to the upper portion 3 of the tube and contains a cross member that acts as a guide for shaft 5. Line 7 is attached to shaft 5 and is used to retrieve the device after a sample is taken and to assist in toggling the shaft and stopper between open and closed positions. Line 6 is attached to top head 8 and is used to lower the device when in the opened position, into a body of fluid to a desired depth.

Figure 2:
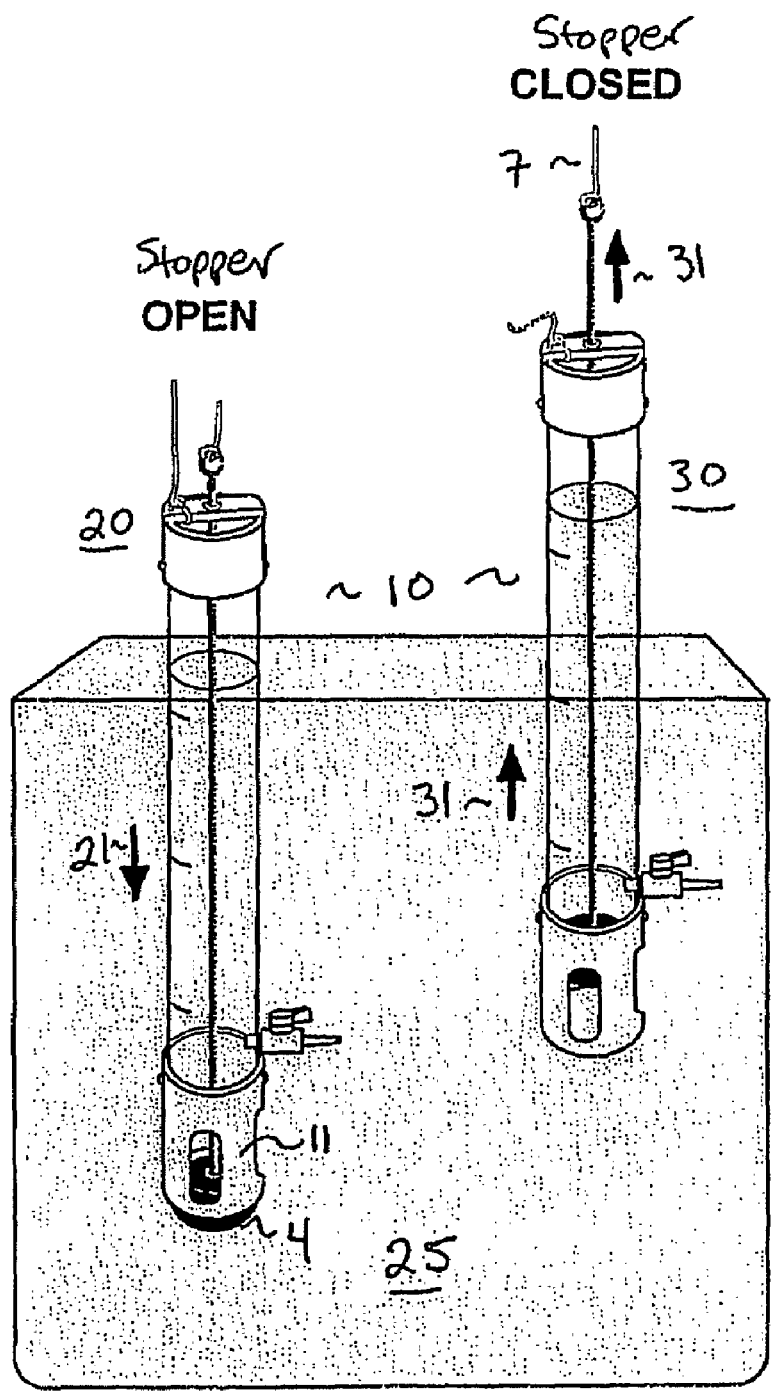
FIG. 2 schematically shows the integrated sampling technique of my invention.

FIG. 2 illustrates operation of my invention for collecting a vertically integrated sample. View 20 shows device 10 being lowered in direction 21 into a body of fluid 25 with stopper 4 in the open position. As soon as the device breaks the surface of body of fluid 25, fluid enters the slots of sleeve 11 and begins to fill the tube. As the device continues in direction 21 more and more fluid 25 enters the tube. Once a desired depth is reached, as illustrated by view 30, line 7 is pulled in direction 31 which in turn moves the shaft and causes stopper 4 to reach a closed position thus preventing any further fluid from entering the tube. Line 7 is further pulled in direction 31 until the device is completely removed from body of fluid 25.

Figure 3:
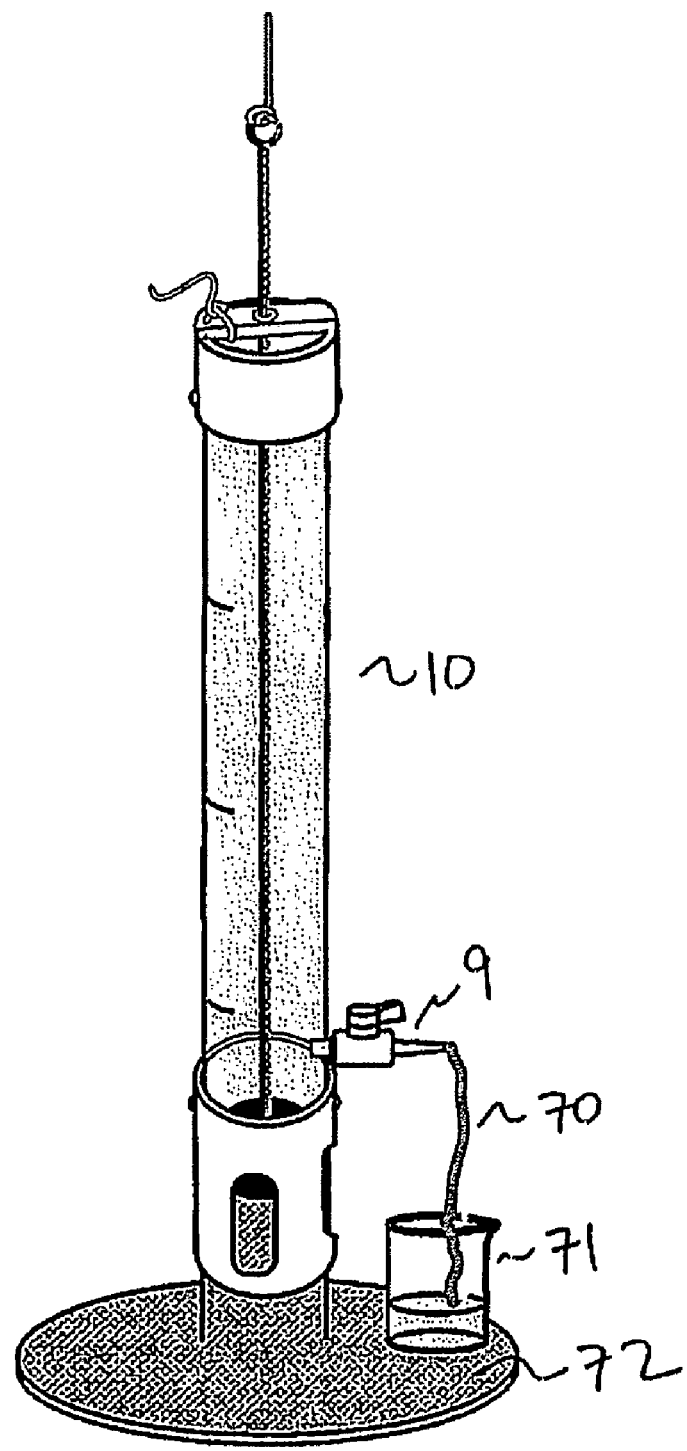
FIG. 3 schematically shows sub-sampling of a fluid collected using a integrated sample collection method.

FIG. 3 illustrates one method of sub-sampling the fluid collected in device 10 obtained using the integrated sampling technique. First, device 10, full of the fluid sample, is maintained in same vertical orientation that it was during sample collection and placed in deck stand 72. Optional sample port 9 is then opened and fluid 70 is removed to vessel 71 for analysis. Because sample port 9 is located at the bottom end of device 10, the first fluid 70 removed will correspond to the last fluid collected at the deepest depth. Throughout the sub-sampling collection process stopper 4 remains in the closed position.

Figure 4:
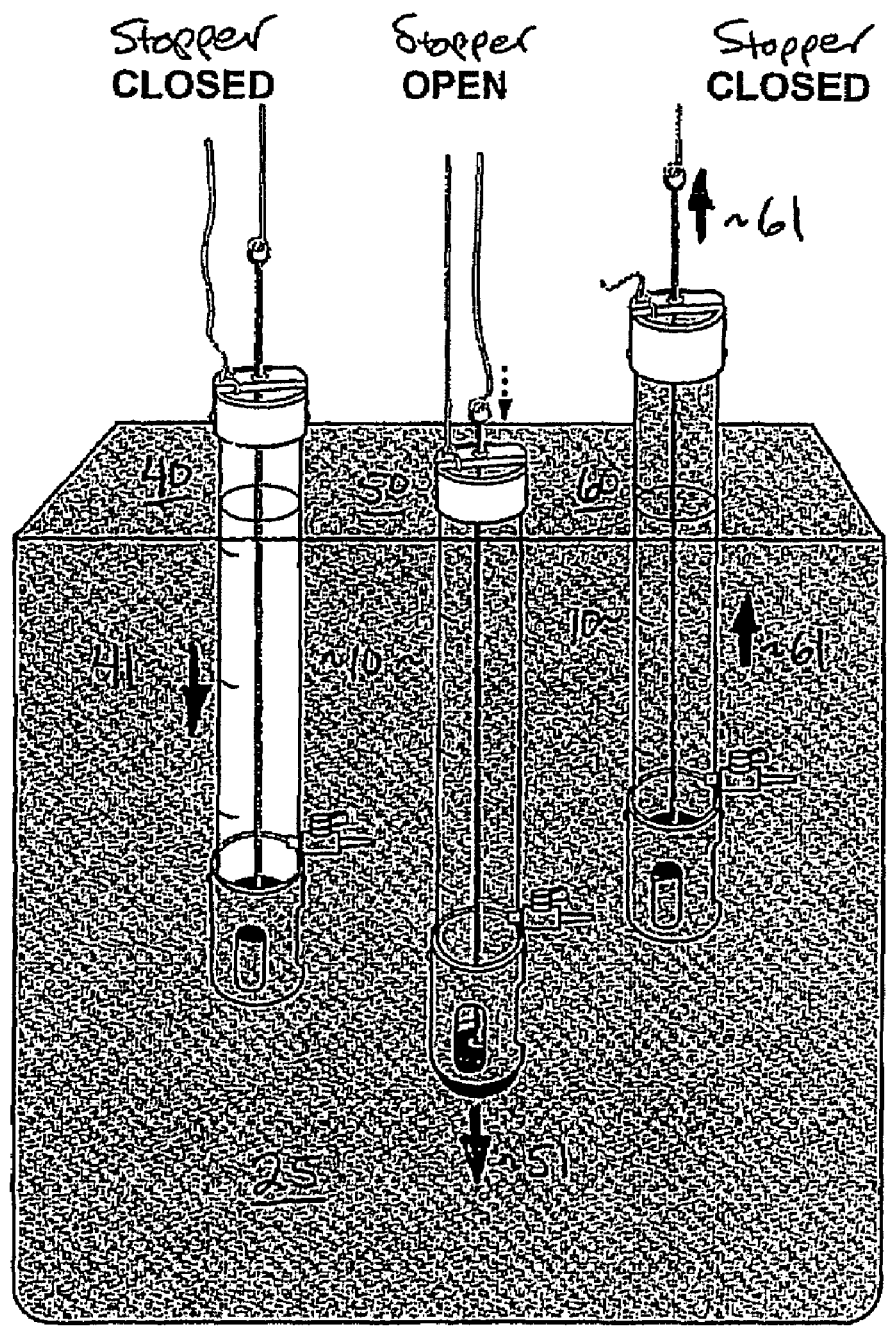
FIG. 4 schematically shows the single-depth point sampling technique of my invention.

FIG. 4 illustrates the "point" sampling technique of my invention. View 40 shows device 10, with the tube empty and with the stopper in the closed position, being pushed into fluid 25 in direction 41 to a predetermined depth. Once at the desired depth, as shown in view 50, the stopper is moved in direction 51 to an open position. Fluid fills the tube and the stopper is then closed. View 60 shows the filled device being retrieved in direction 61 from fluid 25.

Figure 5:
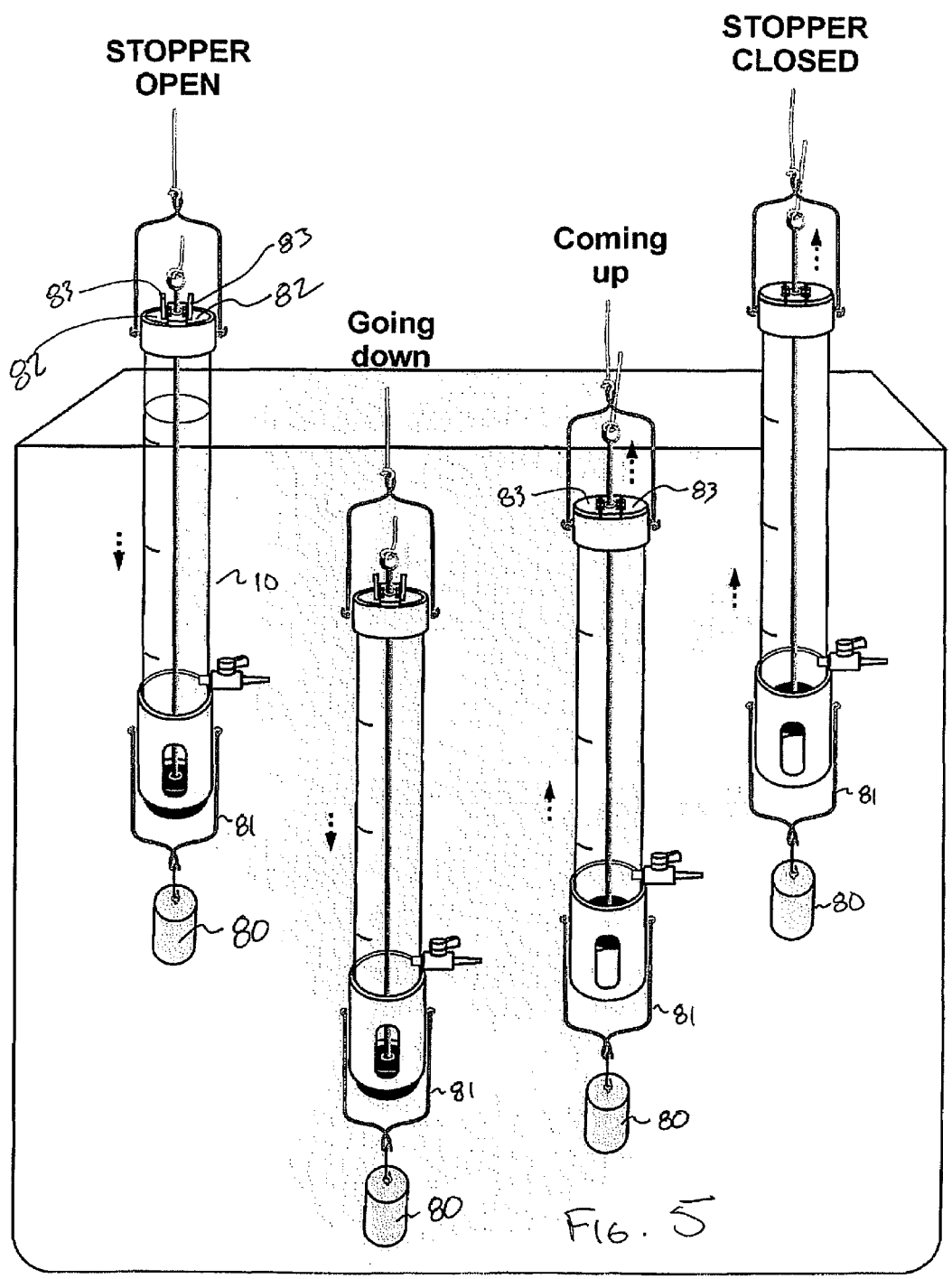
FIG. 5 schematically shows an embodiment collecting an integrated sample of fluid.

FIG. 5 illustrates an embodiment of my invention using an optional ballast 80 attached to device 10 through connector 81. Also shown in this embodiment are optional flaps 83 that remain open during sampling, but closed during retrieval of the device. Flaps 83 automatically close over openings 82 when the sampling device is pulled upward through the body of fluid.

It should be understood that the embodiments and examples disclosed herein are presented for illustrative purposes only and that many other combinations and articles that embody the methods, formulations and systems will be suggested to persons skilled in the art and, therefore, the invention is to be given its broadest interpretation within the terms of the following claims:

I claim:

1. A fully submersible liquid sampling device comprising, in combination,
   a. a tube having a top and bottom and a hollow inside;
   b. a slotted sleeve attached to the bottom of the tube and containing at least one slot that allows liquid to enter inside the tube from the bottom;
   c. a stopper slidably positioned inside the slotted sleeve, where the stopper can be moved from a position that allows liquid to enter the bottom of the tube to a position that prevents liquid from entering the tube;
   d. a shaft operatively connected to the stopper to control the positioning of the stopper, where the shaft is centrally positioned within the hollow and is slidably associated with at least one cross brace;
   e. a sampling port is connected near the bottom of the tube and is in liquid communication with hollow inside of the tube;
   f. flaps connected to the top of the tube that are adapted to automatically close upon retrieval of the sampling device when fully submerged in a body of liquid;
   g. a first line connected to the tube for lowering of and fully submerging the device in a body of liquid; and
   h. a second line connected to the shaft for repositioning the stopper within the slotted sleeve.

2. The sampling device of claim 1 where the tube is constructed of a transparent material to allow a user to visually observe a liquid contained within the tube.

3. The sampling device of claim 1 where the tube contains graduated markings to visually indicate the volume of a liquid contained in the tube or to indicate a sampling depth.

4. A fluid sampling system comprising, in combination,
   a. a tube having a top and bottom and a hollow inside;
   b. a slotted sleeve attached to the bottom of the tube and containing at least one slot that allows liquid to enter inside the tube from the bottom;
   c. a stopper to slidably positioned inside the slotted sleeve, where the stopper can be moved from a position that allows liquid to enter the bottom of the tube to a position that prevents liquid from entering the tube;
   d. a shaft operatively connected to the stopper to control the positioning of the stopper, where the shaft is centrally positioned within the hollow and is slidably associated with at least one cross brace;

e. flaps connected to the top of the tube that are adapted to automatically close upon retrieval of the sampling device when fully submerged in a body of liquid;
f. a first line connected to the tube for lowering of and fully submerging the device in a body of liquid;
g. a second line connected to the shaft for repositioning the stopper within the slotted sleeve;
h. a sampling port connected near the bottom of the tube and in liquid communication with hollow inside of the tube; and
i. a deck stand to support the sampling device in a vertical position while operating the sample port.

5. The system of claim 4 further comprising a removable ballast attached to the bottom of the tube.

6. A method of sampling a body of fluid comprising, in combination,
   a. providing a sampling device having
      i. a tube having a top and bottom and a hollow inside;
      ii. a slotted sleeve attached to the bottom of the tube and containing at least one slot that allows liquid to enter inside the tube from the bottom;
      iii. a stopper to slidably positioned inside the slotted sleeve, where the stopper can be moved from a position that allows liquid to enter the bottom of the tube to a position that prevents liquid from entering the tube;
      iv. a shaft operatively connected to the stopper to control the positioning closing of the stopper, where the shaft is centrally positioned within the hollow and is slidably associated with at least one cross brace;
      v. flaps connected to the top of the tube that are adapted to automatically close upon retrieval of the sampling device when fully submerged in a body of liquid;
      vi. a first line connected to the tube for lowering of and fully submerging the device in a body of liquid;
      vii. a second line connected to the shaft for repositioning the stopper within the slotted sleeve; and
      viii. a sampling port is connected near the bottom of the tube and is in liquid communication with hollow inside of the tube;
   b. repositioning the stopper from a position where liquid cannot enter the tube to a position where liquid can enter the bottom of the tube;
   c. lowering the device into a body of liquid to a predetermined depth using the first line to collect a vertically integrated sample of liquid entering the tube through the slotted sleeve;
   d. repositioning the stopper using the shaft to prevent liquid from entering the tube; and
   e. retrieving the device from the body of liquid.

7. A method of sampling a body of fluid comprising, in combination,
   a. providing a sampling device having
      i. a tube having a top and bottom and a hollow inside;
      ii. a slotted sleeve attached to the bottom of the tube and containing at least one slot that allows liquid to enter inside the tube from the bottom;
      iii. a stopper slidably positioned inside the slotted sleeve, where the stopper can be moved from a position that allows liquid to enter the bottom of the tube to a position that prevents liquid from entering the tube;
      iv. a shaft operatively connected to the stopper to control the positioning of the stopper, where the shaft is centrally positioned within the hollow and is slidably associated with at least one cross brace;
      v. flaps connected to the top of the tube that are adapted to automatically close upon retrieval of the sampling device when fully submerged in a body of liquid;
      vi. a first line connected to the tube for lowering of and fully submerging the device in a body of liquid;
      vii. a second line connected to the shaft for repositioning toggling the stopper within the slotted sleeve; and
      viii. a sampling port is connected near the bottom of the tube and is in liquid communication with hollow inside of the tube;
   b. fully submerging the device with the stopper positioned to prevent liquid from entering the tube a body of liquid to a predetermined depth;
   c. maintaining the device at a constant vertical depth in the body of liquid;
   d. repositioning the stopper by pushing the shaft such that the stopper no longer prevents liquid from entering the tube so as to collect a single-depth point sample of liquid;
   e. repositioning the stopper by pulling the shaft to prevent liquid from entering the tube; and
   f. retrieving the device from the body of liquid using the second line.

8. The method of claim 7 further comprising regulating liquid flow into the tube by partially maintaining closure of the slots in the sleeve by manipulating the stopper with the shaft.

* * * * *